(12) United States Patent
Chung et al.

(10) Patent No.: US 6,755,843 B2
(45) Date of Patent: Jun. 29, 2004

(54) ENDOSCOPIC SUTURING DEVICE

(75) Inventors: Sydney Sheung Chee Chung, Hong Kong (CN); Hitoshi Mizuno, Koganei (JP); Tetsuya Yamamoto, Hidaka (JP); Chika Shiro, Hachioji (JP)

(73) Assignee: Olympus Optical Co., Ltd., Tokyo (JP)

( * ) Notice: Subject to any disclaimer, the term of this patent is extended or adjusted under 35 U.S.C. 154(b) by 0 days.

(21) Appl. No.: 09/964,816

(22) Filed: Sep. 28, 2001

(65) Prior Publication Data

US 2002/0116010 A1 Aug. 22, 2002

Related U.S. Application Data (60) Provisional application No. 60/236,362, filed on Sep. 29, 2000.

(51) Int. Cl.[7] ............................................... A61B 17/04
(52) U.S. Cl. ........................ 606/139; 606/144; 606/148
(58) Field of Search ................................. 606/139, 144, 606/148, 205, 222, 224; 600/104, 121, 123, 153

(56) References Cited

U.S. PATENT DOCUMENTS

| | | | |
|---|---|---|---|
| 3,168,097 A | | 2/1965 | Dormia |
| 5,037,433 A | * | 8/1991 | Wilk et al. .................... 606/139 |
| 5,364,408 A | * | 11/1994 | Gordon ....................... 606/144 |
| 5,374,275 A | * | 12/1994 | Bradley et al. .............. 606/144 |
| 5,437,680 A | | 8/1995 | Yoon |
| 5,470,338 A | * | 11/1995 | Whitfield et al. ........... 606/144 |
| 5,665,096 A | | 9/1997 | Yoon |
| 5,766,186 A | | 6/1998 | Faraz et al. |
| 2002/0116011 A1 | | 8/2002 | Chung et al. |

* cited by examiner

*Primary Examiner*—Julian W. Woo
(74) *Attorney, Agent, or Firm*—Frishauf, Holtz, Goodman & Chick, P.C.

(57) ABSTRACT

An endoscopic suturing includes a suturing device having a curved needle to suture tissue. The endoscopic suturing device also includes a driving means to maneuver the curved needle. The curved needle and the driving means are placed at a distal end of the endoscopic suturing device. The endoscopic suturing device also includes a flexible endoscope connected to the suturing device.

17 Claims, 7 Drawing Sheets

ENDOSCOPIC SUTURING DEVICE

CROSS REFERENCE TO RELATED APPLICATIONS

This application claims priority to provisional application serial No. 60/236,362 filed Sep. 29, 2000.

FIELD OF THE INVENTION

The present invention relates to a suturing device used with an endoscope for suturing a tissue or stanching blood in a body cavity.

BACKGROUND OF THE INVENTION

Endoscopic suturing devices are described, for example, in U.S. Pat. No. 5,037,433, or U.S. Pat. No. 3,168,097, both herein incorporated by reference. Recently, improved endoscopic treatment procedures have developed. Medical treatment may be received without major surgery, such as abdominal section treatment. Because suturing of tissue or stanching of blood after penetration in a body cavity is important, efforts have been made to develop endoscopic techniques.

For example, U.S. Pat. No. 5,037,433 describes a method in which an elongated flexible outer tubular endoscope member has multiple flexible lumens. A flexible endoscope is arranged in one of the lumens. An inner tubular member is arranged in another lumens. A forceps device with forceps in a flexible body portion is arranged in one of the remaining lumens. A curved needle is bent and inserted into the inner tubular member in a slightly stretched state. In addition, the curved needle has a suture member on its proximal end side. For suturing, the curved needle is pushed out from the inner tubular member by pushing the rod members arranged on the distal end of the inner tube, and at the same time, the restoring force is utilized to suture a wound in a body cavity.

U.S. Pat. No. 3,168,097 describes a needle holder used at the time of suturing in a surgical operation. The '097 patent describes a curved needle equipped with a suture at the proximal end that is set in a needle grasping member positioned at the tip of the needle holder. A flexible cable is wound once on the outer circumference of a small coaxial pulley that is fixed to the needle grasping member end. The flexible cable is connected with sleeve through a short rod. The other end is fixed with a turn spring through a short rod, and by maneuvering the curved needle, a lever fixed with a sleeve sutures the wounds in the body while rotating.

Because the device disclosed in '433 patent uses an elastic curved needle inserted in a thin inner tube in a straightly stretched state, the curved needle cannot penetrate deeply into the tissue. The penetrating force is reduced by resistance to the inner tube and the curved needle. The resistance is caused by the restoring power of the curved needle as the curved needle is pushed out from the inner tube by the rod member. In addition, the flexible outer tubular endoscope member may not be bent sufficiently because the rod member has a certain rigidity to push the curved needle from the inner tube. Because the curved needle may not be pressed into the inner tube once the curved needle penetrates the tissue, adjustment may not be made if the curved needle is off target. Moreover, a greater diameter of the flexible outer tubular endoscope member may increase the pain of the patient due to its multi-lumen structure including an endoscope, suturing member, and forceps device.

The '097 patent describes a needle holder originally developed for a surgical operations not suitable for a flexible endoscope. Further, a flexible cable that works the pulley is not firmly fixed to the pulley. Thus, the pulley and the flexible cable slip off when a needle penetrates tissue, and result in a driving force that is not transferred to the needle. After a needle penetrates the body tissue, a lever is released and the righting moment of a spring puts the needle back to the original position. The driving force comes from the spring's flexibility and is insufficient for removing the needle from the body tissue. Moreover, the needle is subject to a force by a spring for the opposite side of the direction of penetration that will decrease the penetrating force when the tissue is penetrated. This effect may result in the body tissue is not being penetrated effectively.

SUMMARY OF THE INVENTION

The present invention offers an endoscopic suturing device that solves the above problems using a flexible endoscope. The effective transfer of the penetrating force occurs despite various bending positions of the endoscope and the adjustment of penetration positions. A smaller outer diameter of the device provides easier maneuvering of the endoscope for suturing. This allows a suturing device to approach the target point of the body tissue easier by maneuvering an endoscope angulation.

The endoscopic suturing device includes a suturing device having a curved needle to suture tissue. The endoscopic suturing device also includes a driving means to maneuver the curved needle. The curved needle and the driving means are placed at a distal end of the endoscopic suturing device. A flexible endoscope is connected to the suturing device.

According to an embodiment of the present invention, an endoscopic suturing device lets a suture pass through a suturing suture hole positioned near the end of a curved needle. The device inserts a grasping forceps via a forceps channel of an endoscope and brings the suture into the proximal end of the endoscope via the forceps channel. At this time, the proximal end of a suturing device will also be inserted from the distal end of a forceps channel into the flexible endoscope. Further, a protective member is arranged at the distal end of the flexible endoscope so that the curved needle of the suturing device will not injure the human body when the suturing device is inserted into a body cavity.

The endoscopic suturing device also inserts into a suture point in the body cavity a suturing device that has been set into an endoscope.

The device maneuvers the rotating maneuvering member of the curved needle, rotates the needle and penetrates the curved needle into the suturing point. Via another channel of an endoscope or an outer channel, the device uses a suture-grasping member to hold and bring an end of the suture protruding from the tissue to the proximal end. The device forms a knot by the two withdrawn sutures and uses a knot pusher to push the knot to the point of a suturing position via the said channel of an endoscope or outer channel and repeat the suturing operation for several times.

DETAILED DESCRIPTION

According to an embodiment of the present invention, an endoscopic suturing device is disclosed. The endoscopic suturing device includes a suturing device having a curved needle to suture tissue. The endoscopic suturing device also includes a driving means to maneuver the curved needle. The curved needle and driving means are placed at a distal end of the endoscopic suturing device. A flexible endoscope is connected to the suturing device.

Figure 1:
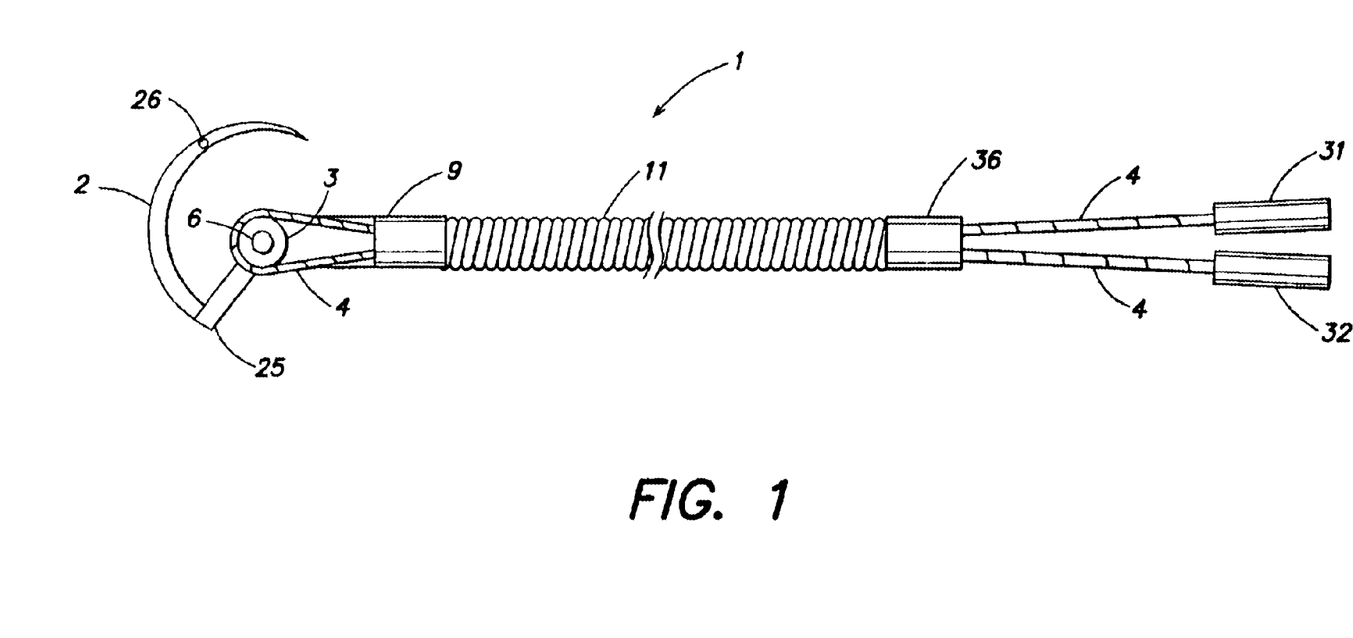
FIG. 1 illustrates a suturing device in accordance with an embodiment of the present invention.
Figure 2:
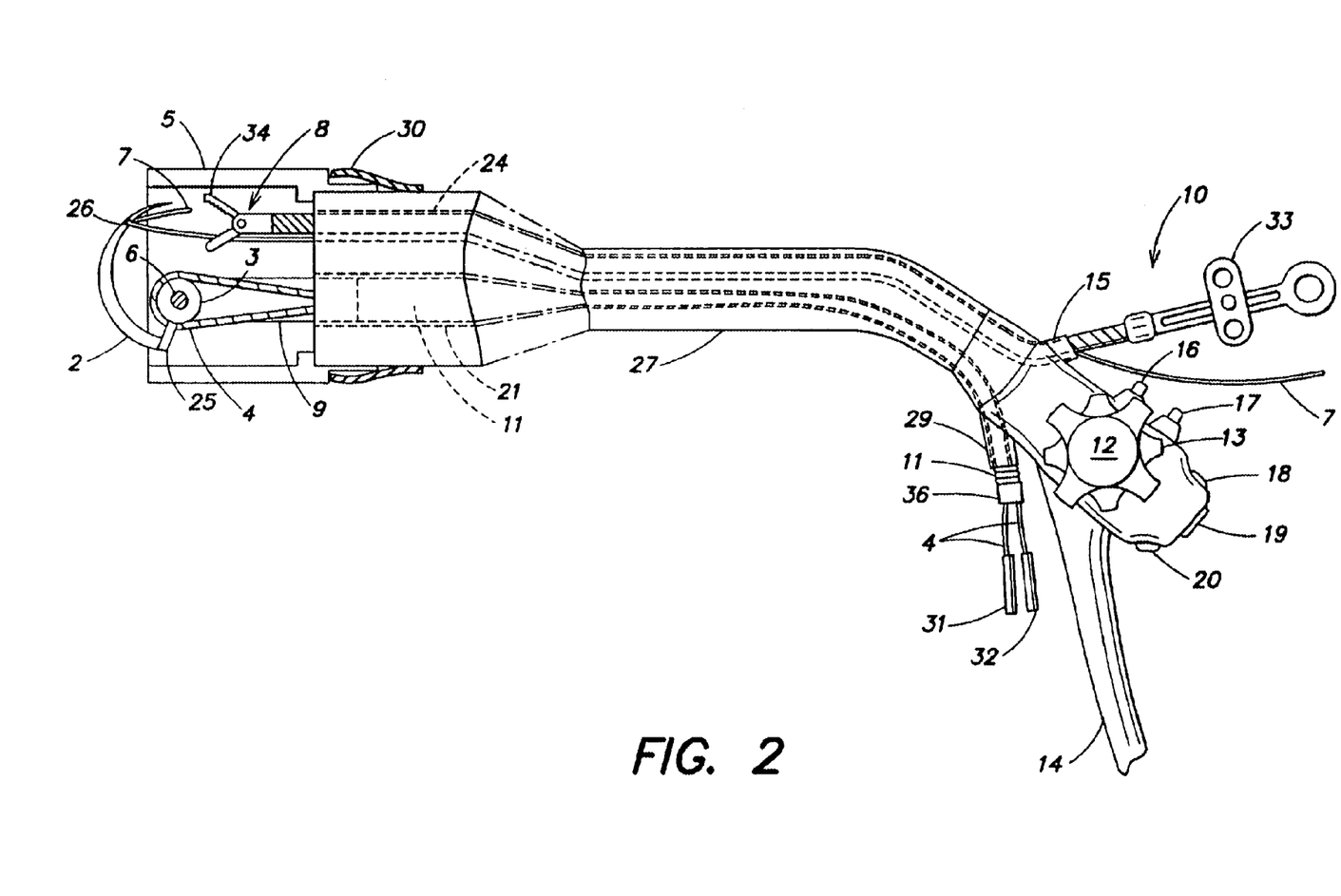
FIG. 2 illustrates a flexible endoscope combined with the suturing device of FIG. 1.
Figure 3:
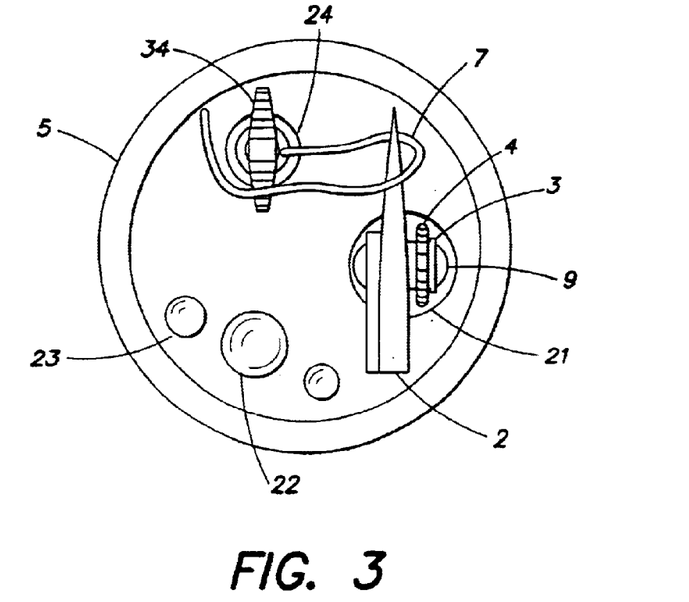
FIG. 3 illustrates a rear view of the flexible endoscope of FIG. 2.
Figure 4:
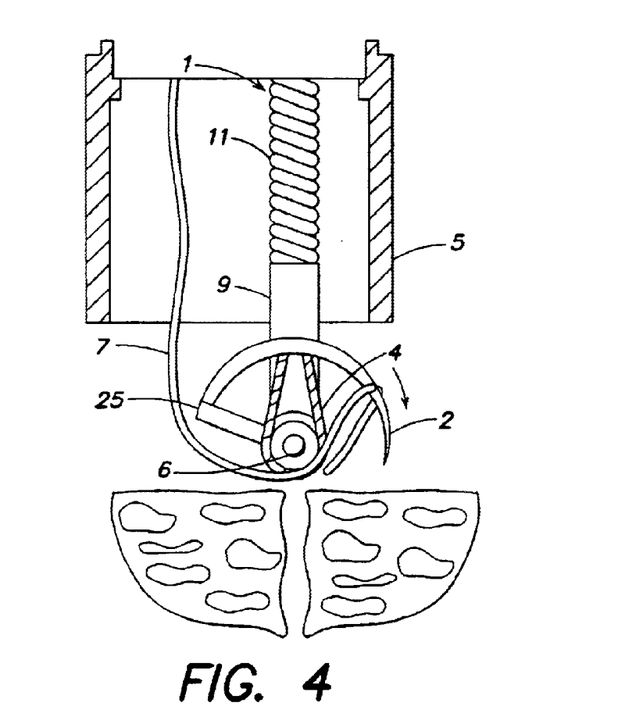
FIGS. 4–14 illustrate the suturing procedures in accordance with an embodiment of the present invention.
Figure 14:
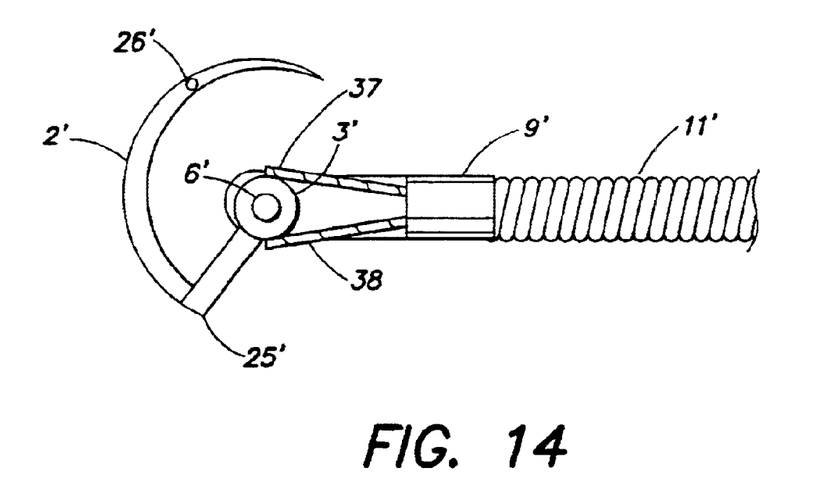
Figure 15:
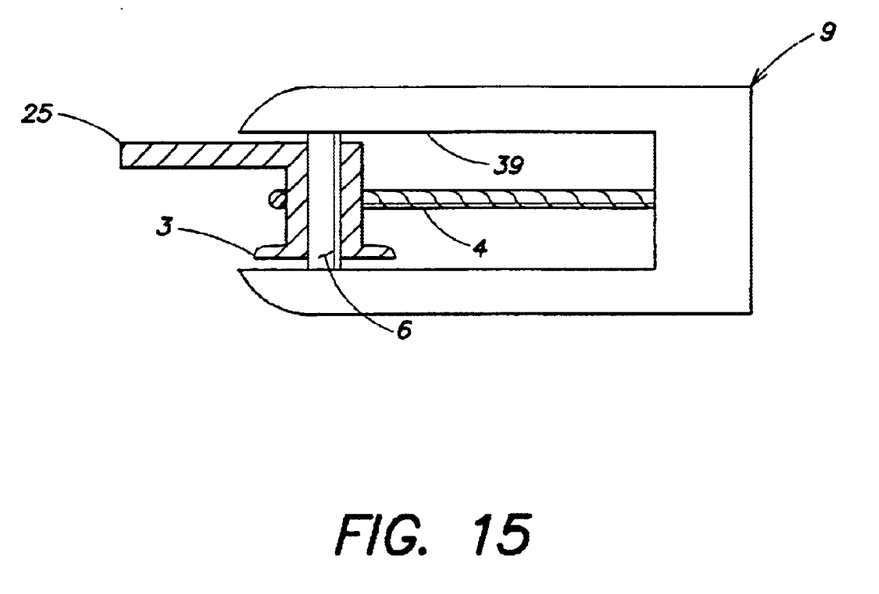
FIG. 15 illustrates a top view of the tip part of the suturing device of FIG. 1.

FIG. 1 depicts a suturing device 1. FIG. 2 depicts a flexible endoscope 27 combined with the endoscopic suturing device 1 of FIG. 1. FIG. 3 depicts a rear view of flexible endoscope 27. FIGS. 4–13 depict the suturing process according to an embodiment of the present invention. FIG. 14 depicts a different configuration of the rotation disc 3 and the operating wire 4. FIG. 15 depicts a top view of the tip part of suturing device 1.

According to FIGS. 2 and 3, flexible endoscope 27 includes CCD camera 22, light guide 23, forceps channel 24, handle 12 that maneuvers the bending section of flexible endoscope 27, handle 13, suction button 17, and air/water supply button 16, video button 18, shutter button 20, image enlarging button 19, air/water supply tube, light guide, suction tube, universal 14 containing various cords for photographing, and channel opening 15. In the present embodiment, a videoscope with a CCD is used, but, alternatively, a fiberscope with eyepieces may be used. Protective member 5 is pressed detachably in the distal end of a flexible endoscope 27 by elastomer member 30 comprised of elastomer group resin.

Referring to FIGS. 1 and 15, a suturing device 1 comprises the supporting member 9 fixed at the distal end of a flexible coil 11 that is arranged as a lumen. A sleeve member 36 is arranged as a lumen and fixed at the proximal end of coil 11. An operating wire 4 passes through sleeve member 36 and coil 11. Referring to FIG. 15, a slit member 39 is located at the distal end of the supporting member 9. A rotation disc 3 that can rotate curved needle 2 is located between the slit member 39 and is arranged on axis 6. Both ends of axis 6 are fixed to supporting member 9. Curved needle 2 is attached to rotation disk 3 via an arm 25. Operating wire 4 for rotating disk 3 is interlinked with part of rotation disk 3 by brazing, soldering, or friction. Further, the proximal end of wire 4 is fixed to curved needle operating members 31 and 32. Operating members 31 and 32 can maneuver curved needle 2 by pushing and pulling. Therefore, appropriate maneuvering of operating members 31 and 32 will make it possible to achieve the proper rotation of curved needle 2.

Referring to FIG. 1, curved needle 2 has a small-diameter hole 26 at its sharp edge side. Referring to FIGS. 2 and 3, a suture 7 is passed through hole 26. The proximal end of suture 7 extends from the coelome via forceps channel 24.

A suture grasping/withdrawing means 8 is placed detachably inside endoscopic suturing device 1 so that part of suture 7 is held after curved needle 2 penetrates the tissue and taken out the body cavity. Although the grasping forceps is used in the disclosed embodiment, any appropriate tool may be used for the grasping and withdrawing procedures. In addition, suture grasping/withdrawing means 8 is situated at an appropriate location to grasp an end of suture 7. Further, suture 7 runs along the inside of forceps channel 24 with suture grasping/withdrawing means 8. In addition, a slider 33 is attached to the suture grasping control section 10. Grasping members 34 may be opened or closed to grasp suture 7 by pushing or pulling slider 33.

FIGS. 1–3 depict the method to set suturing device 1 into a flexible endoscope 27. Protective member 5 is located at the distal end of endoscope 27. Suture grasping control section 10 is inserted into forceps opening 29. Suture grasping control section 10 holds curved needle operating members 31 and 32 and pulls curved needle operating members 31 and 32 from forceps opening 29. Suture 7 previously will have been passed through hole 26. Suture grasping control section 10 is inserted through forceps opening 15, grasps an end of suture 7, pulls suture 7 to said opening 15 and extends suture 7, as depicted in FIG. 2.

Figure 5:
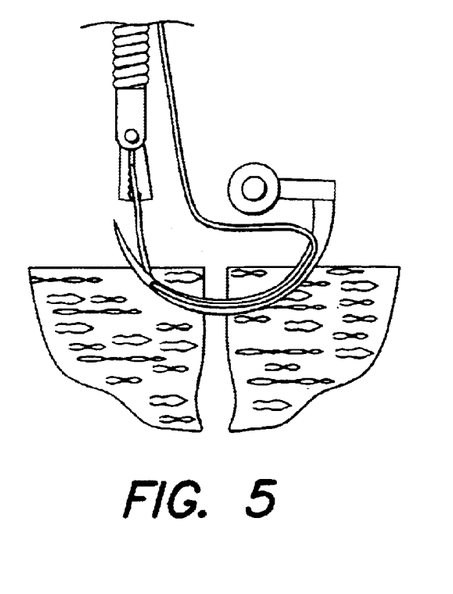
Figure 6:
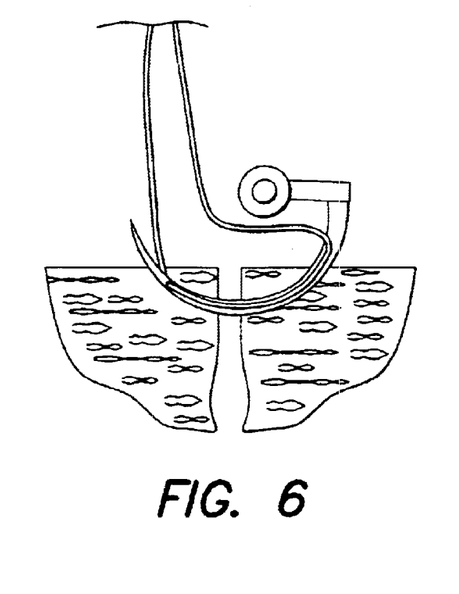
Figure 7:
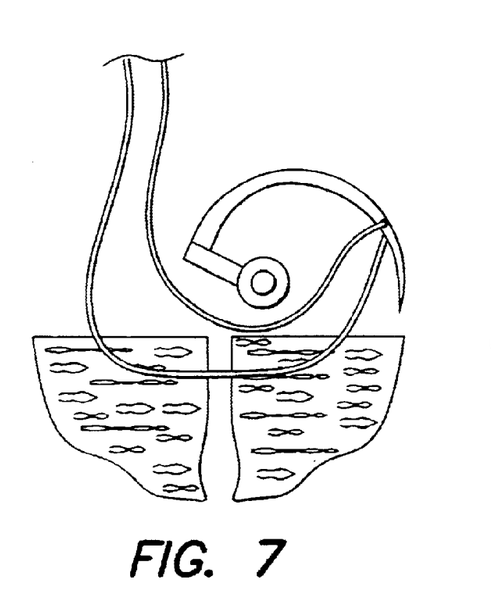

FIGS. 4–13 depict the suturing procedures in accordance the present invention. Endoscope 27 is equipped with suturing device 1 and inserted at a curved position for to suturing. By pulling curved needle operating member 31, disk 3 rotates in one direction, and places curved needle 2 into the position depicted in FIG. 4. By pulling curved needle operating member 32, disk 3 rotates in an opposite direction, and curved needle 2 will penetrate the subject part of suturing, as depicted in FIG. 5. An end of suture 7, after coming out of the tissue, is held by suture grasping/withdrawing means inserted from forceps channel 24. As depicted in FIG. 6, an end of suture 7 is brought outside the body cavity. Curved needle 2 is rotated as depicted in FIGS. 7 and is pulled out of the tissue.

Figure 8:
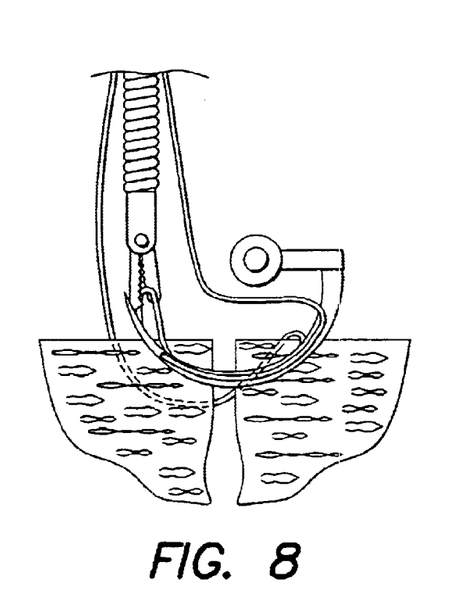
Figure 9:
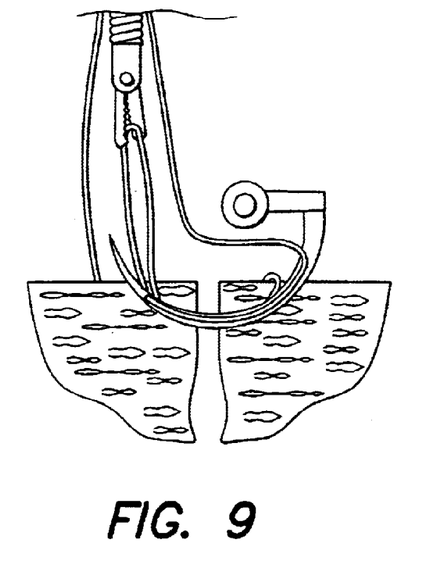
Figure 10:
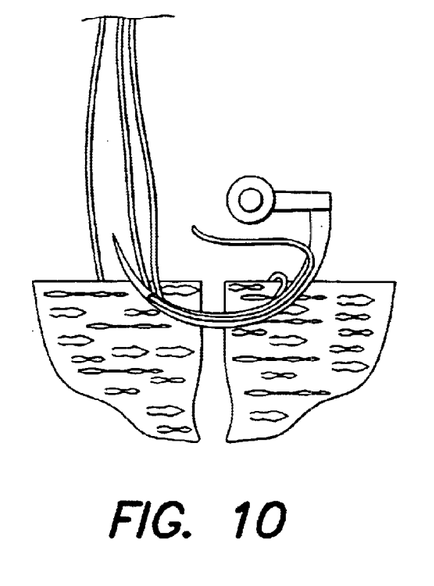
Figure 11:
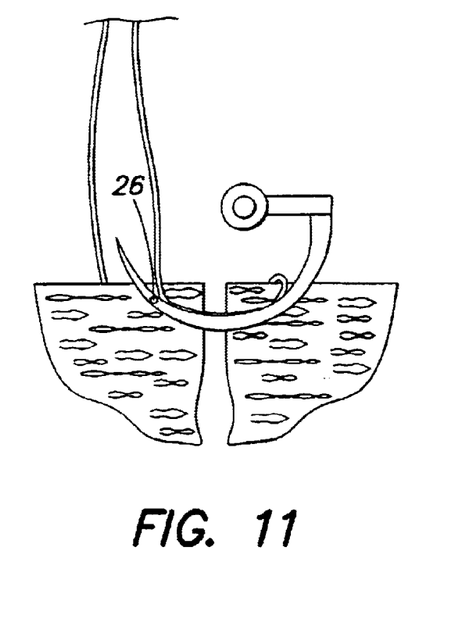
Figure 12:
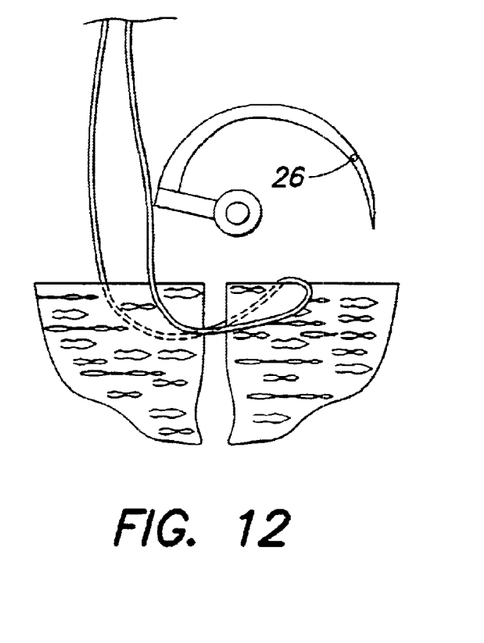

As depicted in FIG. 8, curved needle 2 is placed into a location near the sutured point by angling the scope. As depicted in FIGS. 9–11, another end of suture 7 is brought out from the body cavity without pulling the portion used for suturing. As depicted in FIG. 12, curved needle 2 is pulled from the tissue.

Figure 13:
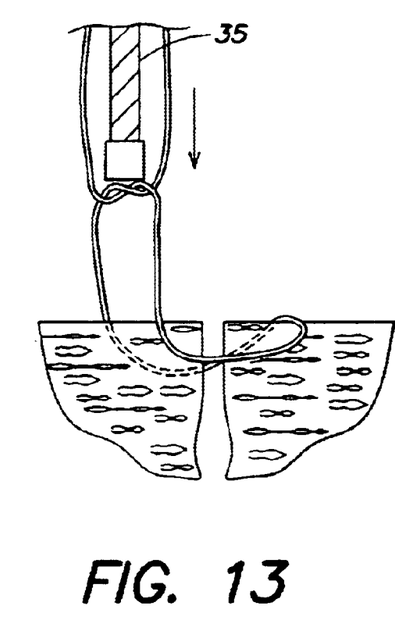

As depicted in FIG. 13, the two end portions of suture 7 brought out from the body cavity are knotted, and the knot is pushed to the sutured region through forceps channel 24 by a knot pusher 35. The suturing process is completed after repeating this procedure several times so as to not loosen the knot.

According to the disclosed embodiments, at any bending condition of a flexible endoscope, the stitching force can effectively be transferred. Therefore, a curved needle can penetrate into tissue in depth for improved stitching force. Also, a suturing device may take advantage of a forceps channel of an endoscope so that the suturing process can be achieved even in the limited space of the body cavity. Furthermore, treatment using general purpose endoscopes may reduce cost. The present suturing device can wash, disinfect, and sterilize like current endoscope accessories so that the suturing device may operate independently.

The penetrating force can be transmitted efficiently to the curved needle even though the endoscope is in any bending position. The suturing process can be achieved even in the limited space of the body cavity so that the suturing device can be used through a forceps channel of an endoscope. The suturing device can be approached to the target region by manipulating the endoscope. Because the control section of the suturing device is arranged near the control section of endoscope, the manipulability of the suturing device and the endoscope may be improved. The curved needle can be inserted to the target region without injuring the body cavity so that the suturing device is combined with an endoscope attached to the protective member. It is possible to adjust the point of penetration. Because the needle is curved, the depth of sticking can be adjusted by switching the curvature radius of needle. Suturing can be made in the tangent direction and front direction in relation to the field of view of endoscope.

In all of the above embodiments, after the suture 7 is passed through the tissue, a knot is tied in the following manners:

For example, the distal end of the suture 7 is grasped by clamp forceps or the like and is withdrawn toward the proximal side through a channel provided within, or along the periphery of, the endoscope. Then the suture 7 is knotted, and the knot is moved by a pusher tube or the like toward the distal end of the endoscope through the channel to bind the tissue by the suture 7. Tying the knot may be repeated several times.

Instead of tying a knot, the suture 7 withdrawn toward the proximal side may be passed through a tube of rubber, and the tube of rubber is moved toward the distal end of the endoscope to bind the tissue. The tube of rubber may be replaced with a clip.

Further, clamp forceps may be inserted into the channel of the endoscope toward its distal end to tie a knot there to bind the tissue.

In each of the above manners, after the tissue has been bound, suture cutting forceps are inserted into the channel of the endoscope toward its distal end to cut a remaining part of the suture 7 while observing with the endoscope.

Although various embodiments are specifically illustrated and described herein, it will be appreciated that modifications and variations of the present invention are covered by the above teachings and within the purview of the appended claims without departing from the spirit and intended scope of the invention.

What is claimed is:

1. An endoscopic suturing device comprising:
    a needle provided at a distal end of said endoscopic suturing device and adapted to suture a tissue of a body;
    a driving mechanism including a flexible wire to rotate said needle;
    a flexible endoscope connected to said suturing device; and
    a connecting member which connects between the distal end of said suturing device and a proximal end of said suturing device, and which comprises a flexible tubular elongated member in which said flexible wire of said driving mechanism is inserted.

2. The endoscopic suturing device of claim 1, wherein said driving mechanism produces rotary motion of the needle; and
    wherein said needle includes at least one perforation through which a suture is passed for performing a suturing operation.

3. The endoscopic suturing device of claim 1, wherein said driving mechanism produces a rotary motion which is controlled in a forward direction and a backward direction.

4. The endoscopic suturing device of claim 1, wherein said needle includes at least one perforation through which a suture is passed for performing a suturing operation.

5. The endoscopic suturing device of claim 4, wherein said perforation is arranged near a sharp-edged portion of said needle.

6. The endoscopic suturing device of claim 1, wherein a rotation axis of said needle is substantially orthogonal to a longitudinal axis of said endoscope.

7. An endoscopic suturing device comprising:
    a needle rotatably provided at a distal end of said endoscopic suturing device and adapted to suture a tissue of a body;
    an axis member provided along a rotational axis of said needle;
    an arm member coupling said axis member and said needle;
    a driving mechanism including a flexible wire which is coupled to said axis member and which rotates said needle; and
    a flexible endoscope connected to said suturing device.

8. An endoscopic suturing device according to claim 7, wherein:
    the driving mechanism operates the needle in a direction for piercing the living body by pulling one end of the flexible wire.

9. An endoscopic suturing device comprising:
    a needle provided at a distal end of said endoscopic suturing device and adapted to suture a tissue of a body;
    a driving mechanism to maneuver said needle, said driving mechanism comprising at least one wire;
    a flexible endoscope connected to said suturing device; and
    at least one cylindrical member arranged to wind said at least one wire.

10. An endoscopic suturing device comprising:
    a needle provided at a distal end of said endoscopic suturing device and adapted to suture a tissue of a body;
    a driving mechanism to maneuver said needle, said driving mechanism comprising at least two wires; and
    a flexible endoscope connected to said suturing device.

11. An endoscopic suturing device comprising:
    a needle provided at a distal end of said endoscopic suturing device and adapted to suture a tissue of a body;
    a driving mechanism to rotate said needle;
    a flexible endoscope connected to said suturing device; and
    a connecting member which connects between the distal end of said suturing device and a proximal end of said suturing device, and which comprises a flexible and tubular member configured to pass through a forceps channel of said flexible endoscope,
    wherein the needle is attached at a distal end of said flexible and tubular elongated member.

12. An endoscopic suturing device comprising:
    a needle provided at a distal end of said endoscopic suturing device and adapted to suture a tissue of a body;
    a driving mechanism to maneuver said needle;
    a flexible endoscope connected to said suturing device; and
    a connecting member which connects between the distal end of said suturing device and a proximal end of said suturing device, and which comprises a flexible and elongated member configured to pass through a forceps channel of said flexible endoscope,
    wherein said flexible and elongated member comprises coils.

13. An endoscopic suturing device comprising:
    a needle provided at a distal end of said endoscopic suturing device and adapted to suture a tissue of a body;
    a driving mechanism to rotate said needle;
    a flexible endoscope connected to said suturing device, and
    an elongated member which supports said needle and which is movable in a longitudinal direction of the flexible endoscope;

wherein said flexible endoscope includes a protective member covering at least part of said needle at a distal end of said flexible endoscope.

14. An endoscopic suturing device comprising:

a needle provided at a distal end of said endoscopic suturing device and adapted to suture a tissue of a body;

a driving mechanism to rotate said needle;

a flexible endoscope connected to said suturing device;

a flexible and elongated member with a proximal and distal end, said needle being disposed on the distal end of the flexible and elongated member; and an outer channel through which at least a part of said flexible and elongated member is insertable.

15. A suturing device adapted for use with a flexible endoscope, comprising:

an elongated flexible member adapted to be arranged along the flexible endoscope from a distal end to a proximal end thereof;

a needle for holding a suture for suturing a tissue of a body and rotatably arranged at a distal end of the elongated member; and a driving mechanism for rotating the curved needle.

16. A suturing device adapted for use with a flexible endoscope, comprising:

an elongated flexible member adapted to be arranged along the flexible endoscope from a distal end to a proximal end thereof;

a needle which is coupled to a rotation axis of the elongated flexible member at a distal end of the elongated flexible member, and which is rotatable around the rotation axis in a direction to pierce a living body tissue, said needle being adapted to hold a suture for suturing the living body tissue; and a flexible wire which is arranged along the elongated flexible member and which applies torque to the needle for rotation.

17. An endoscopic suturing device comprising:

a flexible endoscope having an observation unit at a distal end portion thereof;

a needle rotatably provided forward of the observation unit for holding a suture for suturing a tissue of a body;

a driving mechanism to rotate the needle;

an axis member provided along a rotation axis of the needle;

an arm member coupling the axis member and the needle; and a protective member comprising a cylindrical member attached at the distal end portion of the flexible endoscope for covering at least a part of the needle so as to prevent undesired piercing of the tissue to be sutured.

* * * * *